United States Patent [19]

Mast et al.

[11] Patent Number: 5,127,414
[45] Date of Patent: Jul. 7, 1992

[54] SCUPTURED NAILS

[75] Inventors: Rolf Mast, Chino; Margot Taub, Long Beach; Kris Schmidt, El Monte, all of Calif.

[73] Assignee: Lee Pharmaceuticals, Inc., South El Monte, Calif.

[21] Appl. No.: 82,836

[22] Filed: Aug. 6, 1987

[51] Int. Cl.$^5$ .............................................. A45D 9/00
[52] U.S. Cl. ..................................... 132/73; 132/73.5
[58] Field of Search .............................. 132/7, 73, 73.5

[56] References Cited

U.S. PATENT DOCUMENTS 4,687,827  8/1987  Russo ................................... 132/73

Primary Examiner—Vincent Millin
Attorney, Agent, or Firm—Joseph E. Mueth

[57] ABSTRACT

The combination of a fingernail having adhered to the surface thereof and providing a smooth surface, a coating formed from a polymer of an acrylic monomer, a hydrocarbon solvent and a wax. The acrylic monomer can be acrylic or methacrylic. The solvent can be an alkane or alkene having 6 to 8 carbon atoms. The wax can be paraffin. Also included into the composition can be added an antioxidant and/or thickening agent.

The novel method which comprises applying to a fingernail a liquid composition containing an acrylic monomer, a hydrocarbon solvent, and a wax, and allowing the composition to dry to form an adherent polymeric coating.

The fingernail may be the natural fingernail alone, or together with an artificial fingernail extension.

38 Claims, 1 Drawing Sheet

SCUPTURED NAILS

BACKGROUND OF THE INVENTION

In the prior art, it is known that nail tips are glued onto the end of the natural fingernail with instant nail glue. A room temperature curing acrylic overlay is then brushed over the top in order to form a continuous ridge-covering film. An acrylic overlay essentially consists of an acrylic monomer which contains an accelerator, which is mixed with a peroxide catalyst dispersed in an acrylic polymer just prior to use, and thus sets into a hardened resin.

The use of room temperature curing acrylics to lengthen natural fingernails is well-known. See for example Lee and Orlowski U.S. Pat. No. 4,104,333 and Orlowski U.S. Pat. No. 4,495,172. Patents exist where the acrylic is brushed over a removable underlying form (Slack U.S. Pat. No. 2,799,282), as well as with different plastic co-extenders (Noskin U.S. Pat. No. 3,786,821 and Jarby U.S. Pat. No. 3,502,088). Similarly, the use of nail tips to lengthen nails is well known (see for example Matranga and Hokama U.S. Pat. No. 4,135,526). To those skilled in the art it has become common knowledge to apply acrylic resins over glues on nail tips as one convenient way to artificially lengthen nails. In spite of a large amount of commercial and scientific activity in this field one problem with the acrylic overlay persists. This is the problem of oxygen inhibition. The problem with the prior art just discussed is one of oxygen inhibition which- causes the top surface of the coated nail, that is, the overlay not to dry. More volatile, and thus more toxic monomers suffer less from this problem, but it is very desirable to refrain from the use of such materials with nail tips to avoid toxicity problems. The present invention concerns a solution to this dilemma. This background will not deal comprehensively with the body of work done in attempts to solve this problem, which is prevalent not only with acrylics but with other types of resins also. One solution that has been proposed, however, is central to this invention. That is the use of waxes to prevent the oxygen inhibition. The pertinent literature here is now discussed.

T. L. Phillips, British Plastics, February 1961, p. 69 "Polyester resins for coating applications" discloses a peroxide-initiated cure of a styrene/polyester mixture. This paper states that somewhere in the range of 0.001 to 3% by weight of a paraffin wax will eliminate the oxygen inhibition of surface curing. S. H. Schroeter and J. E. Moore in "The ultraviolet cure of solventless resins—pollution free method?", Nonpolluting Coatings and Coating Processes, J. L. Gordon and J. W. Prane, Eds., Plenum Publishing, New York, 1973, p. 135. Photoinitiation of resin cure is a well-known and common technique which is applied to acrylic and other resins in this paper. A variety of different waxes were found to have different degrees of effectiveness in stopping oxygen inhibition. These included Chlorowax, Naprowax, Acrawax, Epolene wax, carnauba wax, beeswax, ceresine wax, Oxazoline wax, stearic acid, stearyl methacrylate, methyl stearate, paraffin waxes and mineral oil. Of these the most effective, and materials of choice, were the straight-chain hydrocarbon paraffin waxes.

D. A. Bolon and K. K. Webb, J. App. Polymer Sci., Vol. 22, 2543-2551 (1978) "Barrier coats versus inert atmospheres. The elimination of oxygen inhibition in free-radical polymerizations." This discusses the effect of paraffin waxes of different melting points on the oxygen inhibition of different acrylics. They were effective in concentrations of around 1% by weight. Also the higher the temperature of the reaction, the higher the melting point of the wax that is needed. Nakao et al., Japan Kokai Tokyo Koho, 79 46,240 "Unsaturated polyester coating materials". Compositions contain a wax, polyester, and solvent to prevent oxygen inhibition. The only reason for mentioning this patent is that their use of the term "solvent" is totally different to the one used below in this disclosure. In this patent the term "solvent" refers to the reactive styrene moiety that is part of the polyester polymerization system, and the work is essentially no different from that of T. L. Phillips above.

Even with all the above elements already known we have found, as explained below, that the simple addition of wax to a standard acrylic nail extender did not satisfactorily prevent oxygen inhibition. Thus, it is not possible to make an acrylic overlay which could be brushed onto a natural nail, or a natural nail/nail tip combination as a relatively thin film that would dry to the necessarily completely dry surface, especially with the higher molecular weight and lower toxicity acrylic monomers as described in U.S. Pat. No. 4,104,333.

In addition to the oxygen inhibition problem there are two other disadvantages in the current art which this invention seeks to overcome. After the current formulations have hardened, they have a strong tendency to turn yellow. Also during application they are stiff and difficult to use and the subsequent coating is difficult to file and finish. The basic reason for this is in the recommended mode of application. The liquid acrylic monomer, containing a room temperature accelerator, is mixed with an acrylic polymer containing benzoyl peroxide catalyst. The normally recommended mixing ratio is in the range of 1:1 to 1:2 parts by weight of liquid to powder. This excessive powder makes stiff, difficult to work with mixtures.

The compositions described below greatly minimize these disadvantages. According to the present invention, it has become possible to use much less powder, resulting in easier to brush mixtures with less benzoyl peroxide and consequently less yellowing of the final product.

SUMMARY OF THE INVENTION

The combination of a fingernail having adhered to the surface thereof and providing a smooth surface, a coating formed from the polymer of an acrylic monomer, a hydrocarbon solvent, and a wax.

The novel method which comprises applying to a fingernail a liquid composition containing an acrylic monomer, a hydrocarbon solvent, and a wax, and allowing the composition to dry to form an adherent polymeric coating.

It is an object of this invention to provide a novel composition of a natural fingernail, with or without an artificial fingernail extension, having adhered thereto a smooth coating which is without oxygen inhibition problems.

More particularly, it is an object of this invention to provide for the coating of fingernails in a simpler and more effective manner.

These and other objects and advantages of this invention will be apparent from the detailed description which follows.

It has been found that the addition of a wax plus a hydrocarbon solvent, in preferred compositions as described below, allows acrylic based room temperature curing systems to be used without oxygen inhibition problems. It has further been found that within certain concentration limits these systems can be used with more liquid than powder (as defined below) making their application easier.

DESCRIPTION OF THE PREFERRED EMBODIMENT

Turning to the drawings:

FIG. 1 shows the adhesive 10 (which is the acrylic monomer, hydrocarbon solvent, wax mixture) being brush on fingernails 14 before application of nail extensions 12. Adhesive 10 has been pre-mixed from powder and liquid to form a paste in container 18. Adhesive 10 can also be mixed directly on the brush. FIG. 1 also shows where adhesive 10 has dried to an overlay 11, and where two fingernails 14 have been prefitted with nail extensions 12 prior to application of the overlay. Adhesive 10 can be applied over either just nails, or nails and nail extensions. Application of the nail extension 12 to the natural nail 14 may be made with ethyl cyanoacrylate or any other suitable adhesive.

FIG. 2 is a close-up showing the nail extension 12 applied to the natural nail 14 prior to application of the adhesive 10.

Figure 1:
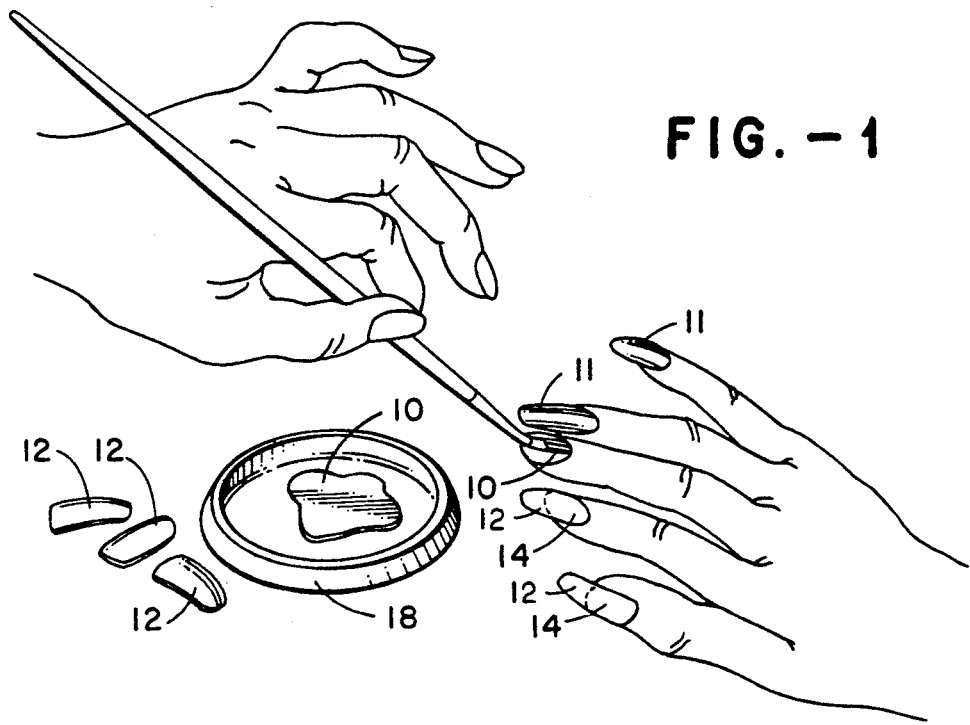

A variety of waxes can be used in the practice of this invention. In practice we have done our work with waxes of different melting points, and the present invention is applicable to any wax that falls in the useful melting point range, and of course paraffin waxes are the preferred waxes. The preferred melting point range is no lower limit up to about 165° F. An especially preferred wax is paraffin wax of melting point of about 125° F.

The hydrocarbon solvents can be either aliphatic or aromatic. If aliphatic, they fall into one of the following formulation types:

where n = 6, 7, or 8.

The preferred aliphatic hydrocarbon is hexane.

If aromatic, the hydrocarbon solvent is preferably either toluene or xylene.

Acrylic monomers, as used in the formulations below, have been well described in the literature. They consist of a monofunctional main monomer together with a polyfunctional cross-linking monomer. Technically acrylic and methacrylic monomers work equally well and both are included in the scope of this invention. Methacrylic monomers, however, are preferred as they are less toxic than the acrylic monomers, and discussion will be restricted to those species. Useful methacrylic monomers are either methacrylic acid or an amide or ester as based on the following structures:

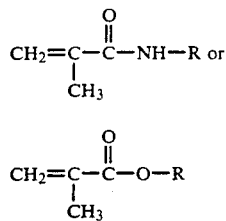

wherein R is any moiety which keeps the molecular weight of the molecule as a whole in the range of from about 115 to about 200. Examples of useful compounds are propyl methacrylate, isopropyl methacrylate, butyl methacrylate, isobutyl methacrylate, hydroxyethyl methacrylate, ethoxyethyl methacrylate, glycidyl methacrylate, tetrahydrofurfuryl methacrylate, dimethylaminopropyl methacrylate, cyclohexyl methacrylate and cyclopentyl methacrylate. This does not cover the full range of acrylics that could be used. Obviously, substituent moieties other than those specifically listed here which do not interfere with or significantly disrupt the intended polymerization reaction are herein contemplated.

In order to achieve the proper consistency in the final product, as is well-known in the art, a second, polyfunctional acrylic based reactive species is necessary. These are generally referred to as cross-linking agents. In practice a wide variety of di- and trifunctional methacrylates could be used as the crosslinking agent. A listing of some preferred crosslinking agents taken from U.S. Pat. No. 4,495,172 and which can be included here is also appended to this disclosure. Additional cross-linking agents which have been found useful are ethoxylated bisphenol A dimethacrylate, trimethylolpropane triacrylate, and neopentylglycol dimethacrylate.

The third essential ingredient in the acrylic liquid of this invention is the accelerator, which is one of a number of amines that allows the reaction to cure rapidly at room temperature in the presence of a suitable catalyst. A description of some preferred accelerators taken from U.S. Pat. No. 4,104,333 is the disclosure of which is incorporated herein by reference.

Two other ingredients that are preferred embodiments of the liquid, but not essential, are an antioxidant to prevent premature polymerization of the product and a thickening agent to allow greater ease of use of the product by the consumer. An antioxidant (or stabilizer) that we find very useful in practice is butylated hydroxytoluene (BHT) at a level of 0.05 to 0.1% by weight based on the total liquid composition.

The preferred type of thickening agent consists of polymers which are significantly soluble in the liquid mixture. Acrylic polymers and copolymers make very suitable thickening agents. Three that are commonly used in this context are polymethyl methacrylate, polyethyl methacrylate, and a copolymer of polyethyl/methyl methacrylate. Another effective thickening agent is the fumed silica type such as Aerosil 380 (a trademark of Degussa Corporation).

The large variety of antioxidants and thickening agents that could be used by those skilled in the art will not be dealt with here.

There are other modifications that could be made to the liquid by those skilled in the art. This includes addition of dyestuffs, minor additions of non-acrylic or high molecular weight acrylic monomers to act as modifiers of physical properties, inert plasticizers, and the addition of minor amounts of materials to further speed reaction times, and/or increase substrate adhesion. For instance, methacrylic acid is used in this context in the common art.

In order to form a room temperature cured coating on the nail, the liquid, which has essential ingredients as described above, is mixed with a powder just prior to application. There are two essential ingredients in the powder. These are a peroxide catalyst in an amount which is effective to initiate the polymerization reaction, and a filler.

The filler is a fine powdered solid that may be soluble, partially soluble, or insoluble in the liquid. Preferred soluble and partially soluble solids include acrylic polymers of the acrylic monomers themselves that were detailed above. Specific examples of preferred fillers are polymethyl methacrylate, polyethyl methacrylate, and copolymer of polyethyl/methyl methacrylate. Inorganic fillers such as finely divided alumina silicates, silica, quartz, glass, and the like may also be used where these materials may or may not have a silanated surface treatment.

The peroxide catalyst is generally benzoyl peroxide. Other peroxides are known to the art and in this work a study of these different possibilities was not made. An example of an alternative catalyst is cumene hydroperoxide. It is known with this material that to be useful as an initiator at room temperature a different accelerator system is necessary. This accelerator is a mixture of a copper salt and acetyl thiourea. It is to be understood that any known accelerator-peroxide combination which is reactive at room temperature could be used in this invention. As benzoyl peroxide was satisfactory, however, no further curing promoters were examined.

Other ingredients known to the art could be added to the powder. These include dyes and pigments and fine particle rubber to decrease the brittleness of the final formula.

The preferred concentration ranges of the preferred components listed above are now given:

|  | Broad Range | Narrow Range |
| --- | --- | --- |
| Liquid Material |  |  |
| Acrylic Monomer(s) | 10.0–93.0 | 50.0–85.0 |
| Crosslinking Monomer | 0.5–50.0 | 3.0–20.0 |
| Wax | 0.01–5.0 | 0.2–3.0 |
| Hydrocarbon Solvent | 0.7–20.0 | 1.0–16.0 |
| Accelerator | 0.1–8.0 | 1.0–5.0 |
| Thickening Agent | 0–20.0 | 0–15.0 |
| Antioxidant | 0–5.0 | 0–0.5 |
| Powder Material |  |  |
| Peroxide Catalyst | 0.5–20.0 | 1.0–8.0 |
| Filler | 99.5–80.0 | 99.0–92.0* |

*These ranges would be adjusted accordingly if other optional ingredients are added.

The liquid and powder compositions are premixed before being brushed onto the nail. The method of premixing is not important. One common method, however, is to apply them both to the same brush, prior to brushing them onto the nail. The broad ranges by weight in which they can be premixed are not an essential feature of this invention and mixing ratios in the broad range of 5 parts liquid: 1 part powder going to 1 part liquid: 3 parts powder can be contemplated.

Mixing ratios of current compositions which overlap the above have been specified. In practice, however, with current state of the art compositions the more powder that is used the less is the problem with oxygen inhibition. The more easily used compositions, therefore, have recommended mixing ratios in the range of 1 part liquid: 2 parts powder if they contain the more volatile and toxic acrylic monomers like ethyl methacrylate, and mixing ratios in the range of 1 part liquid: 1 part powder going to 1 part liquid: 2 parts powder if they contain the less toxic acrylic monomers like tetrahydrofurfuryl methacrylate. With the products of this invention liquid levels of as high as 5 parts liquid to 1 part powder, can be used even with the higher molecular weight acrylic monomers such as tetrahydrofurfuryl methacrylate. Thus an optimum blend of safety and ease of use is possible.

The preferred mixing ratios with the current composition is about 2 parts liquid: 1 part powder to about 1 part liquid: 1 part powder.

Using procedures well-known to the art, the time in which the composition sets after mixing the liquid and powder components is set in the range of about 60 seconds to about 360 seconds simply as a convenience to the person applying the nail and not as an instrumental part of the invention. The set time is regulated by adjusting the amounts of accelerator and catalyst used.

Some preferred examples of the invention:

The following different liquids were prepared by simple mixing techniques:

Figures are in percent by weight:

The following examples illustrate the use levels of wax and hydrocarbon solvent to prevent the oxygen inhibition.

| Material - Liquid | Ex. 1 | Ex. 2 | Ex. 3 | Ex. 4 | Ex. 5 |
| --- | --- | --- | --- | --- | --- |
| THFMA[1] | 66.5 | 73.71 | 64.5 | 61.58 | 76.7 |
| Acrylic copolymer[2] | 10.5 | 10.5 | 12.5 | 10.0 | 10.0 |
| DEGDMA[3] | 10.0 | 8.19 | 10.0 | 9.0 | 10.0 |
| Toluene | 10.0 | 5.0 | 10.0 | 16.0 | 1.3 |
| Paraffin wax[4] | 1.0 | 1.5 | 1.0 | — | 0.4 |
| Paraffin wax[5] | — | — | — | 0.32 | — |
| Accelerator[6] | 2.0 | 1.0 | 2.0 | 2.0 | 1.5 |
| BHT | — | 0.1 | — | 0.1 | 0.1 |

[1]tetrahydrofurfuryl methacrylate
[2]polymethyl/polyethylmethacrylate copolymer
[3]diethyleneglycol dimethacrylate
[4]Aristowax 125 from Union Oil
[5]Aristowax 165 from Union Oil
[6]N,N-bis(2-hydroxyethyl)-p-toluidine With acrylic liquid examples 1 to 5, in each case the following powder was used at a mixing ratio of 2 parts liquid: 1 part powder.

| Material - Powder | % by wt. |
| --- | --- |
| benzoyl peroxide | 3 |
| polymethyl-polyethylmethacrylate copolymer | 97 |

Examples which illustrate the use of different crosslinking agents, accelerator, and hydrocarbon solvent are:

| Material | Ex. 6 | Ex. 7 | Ex. 8 | Ex. 9 |
| --- | --- | --- | --- | --- |
| THFMA | 69.5 | 80.0 | 75.0 | 69.0 |
| Ethoxylated bisphenol A dimethacrylate | 17.5 | — | — | — |

-continued

| Material | Ex. 6 | Ex. 7 | Ex. 8 | Ex. 9 |
|---|---|---|---|---|
| Trimethylolpropane trimethacrylate | — | 7.0 | — | — |
| Trimethylolpropane triacrylate | — | — | 12.0 | — |
| Neopentylglycol dimethacrylate | — | — | — | 18.0 |
| Hexane | 10.0 | 10.0 | 10.0 | 10.0 |
| N,N-dimethyl-p-toluidine | 2.0 | 2.0 | 2.0 | 2.0 |
| Parowax SM | 1.0 | 1.0 | 1.0 | 1.0 |

Parowax SM is a trademark of Amoco Oil Company.

Examples 10 to 12 illustrate other acrylic monomers that can be used.

| Material | Ex. 10 | Ex. 11 | Ex. 12 |
|---|---|---|---|
| Isobutyl methacrylate | — | 82.0 | 72.0 |
| Hydroxypropyl methacrylate | 72.0 | — | — |
| Ethyleneglycol dimethacrylate | 10.0 | — | 10.0 |
| Trimethylolpropane trimethacrylate | — | 10.0 | — |
| Polymethyl/polyethyl methacrylate copol. | 10.0 | — | 10.0 |
| Aristowax 125 | 1.5 | 1.5 | 1.5 |
| Toluene | 5.0 | 5.0 | 5.0 |
| N,N-dimethyl-p-toluidine | 1.5 | 1.5 | 1.5 |

Figure 2:
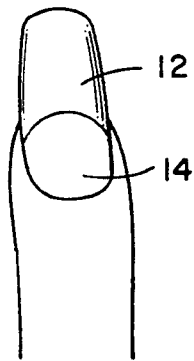
Figure 3:
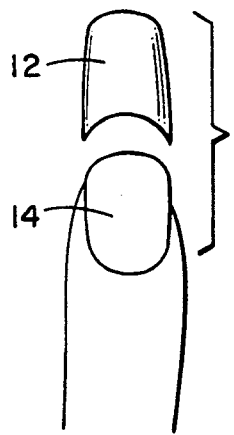
FIG. 3 shows the nail extension 12, and the natural nail 14, prior to application of the former.
Figure 4:
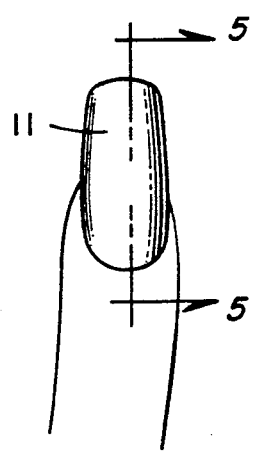
FIG. 4 shows the dried overlay 11, in situ over the nail/nail extension combination of FIG. 2.
Figure 5:
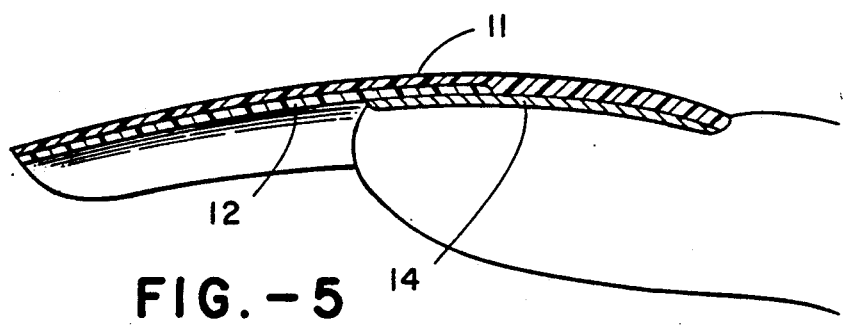
FIG. 5 is a cross-sectional view taken on the line indicated in FIG. 4. This shows the nail extension 12 adhering to the natural nail 14, and both covered with the overlay.

Considering the drawings in more detail, the nail extension 12 can be manually positioned with respect to the natural fingernail 14 as is shown in FIGS. 2 and 3. An adhesive can first be applied to the fingernail 14. This adhesive can be the composition of this invention or any other adhesive adapted to join an artificial nail to a natural nail. Usually, it is the latter, such as a simple cyanoacrylate adhesive. Once the extension 12 is positioned as shown in FIGS. 2 and 3, the upper surface of extension 12 and the exposed fingernail 14 are then coated with adhesive 10. The adhesive hardens by drying to yield a smooth adherent surface coating having the composition of the present invention.

It is to be understood that this invention is also applicable to the case where the composition of this invention is applied to a natural fingernail, and no artificial extension is used.

Having fully described the invention it is intended that it be limited solely by the lawful scope of the appended claims.

We claim:

1. The combination of a fingernail having adhered to the surface thereof and providing a smooth surface, a coating formed from a polymer of an acrylic monomer, a hydrocarbon solvent and a wax.

2. The combination of a fingernail, an artificial fingernail tip and having adhered to the surface thereof and providing a smooth surface, a coating formed from a polymer of an acrylic monomer, a hydrocarbon solvent and a wax.

3. The combination of claim 1 wherein the acrylic monomer is acrylic or methacrylic.

4. The combination of claim 2 wherein the acrylic monomer is acrylic or methacrylic.

5. The combination of claim 1 wherein the acrylic monomer is either methacrylic acid or an amide or ester having the following structures:

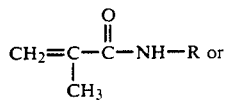

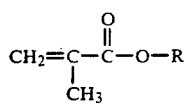

wherein R is an organic radical which provides an overall monomeric molecular weight of from about 115 to about 200.

6. The combination of claim 2 wherein the acrylic monomer is either methacrylic acid or an amide or ester having the following structures:

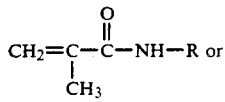

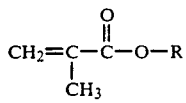

wherein R is an organic radical which provides an overall monomeric molecular weight of from about 115 to about 200.

7. The combination of claim 1 wherein the acrylic monomer includes a polyfunctional acrylate which functions to crosslink said polymer.

8. The combination of claim 2 wherein the acrylic monomer includes a polyfunctional acrylate which functions to crosslink said polymer.

9. The combination of claim 1 wherein the wax has a melting point below about 165° F.

10. The combination of claim 2 wherein the wax has a melting point below about 165° F.

11. The combination of claim 1 wherein the wax is a paraffin.

12. The combination of claim 2 wherein the wax is a paraffin.

13. The combination of claim 1 wherein the solvent is an alkane or alkene having from about 6 to 8 carbon atoms.

14. The combination of claim 2 wherein the solvent is an alkane or alkene having from about 6 to 8 carbon atoms.

15. The novel method which comprises applying to a fingernail a liquid composition containing an acrylic monomer, a hydrocarbon solvent, and a wax, and allowing the composition to dry to form an adherent polymeric coating.

16. The novel method which comprises applying to a fingernail and an artificial fingernail tip a liquid composition containing an acrylic monomer, a hydrocarbon solvent, and a wax, and allowing the composition to dry to form an adherent polymeric coating.

17. The method of claim 15 wherein just prior to application, the liquid composition is mixed with a powder which includes an effective amount of a polymerization catalyst for said monomer.

18. The method of claim 16 wherein just prior to application, the liquid composition is mixed with a powder which includes an effective amount of a polymerization catalyst for said monomer.

19. The method of claim 15 wherein the liquid composition includes a thickening agent.

20. The method of claim 16 wherein the liquid composition includes a thickening agent.

21. The method of claim 15 wherein the liquid composition includes an antioxidant.

22. The method of claim 16 wherein the liquid composition includes an antioxidant.

23. The method of claim 17 wherein the ratio of liquid composition to powder is from about 5 to 1 to about 1 to 3.

24. The method of claim 18 wherein the ratio of liquid composition to powder is from about 5 to 1 to about 1 to 3.

25. The method of claim 17 wherein the powder includes a fine powdered solid filler.

26. The method of claim 18 wherein the powder includes a fine powdered solid filler.

27. The method of claim 15 wherein the acrylic monomer is acrylic or methacrylic.

28. The method of claim 16 wherein the acrylic monomer is acrylic or metacrylic.

29. The method of claim 15 wherein the acrylic monomer is either methacrylic acid or an amide or ester having the following structures:

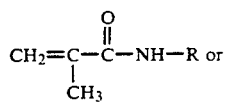

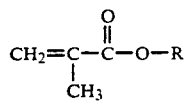

wherein R is an organic radical which provides an overall monomeric molecular weight of from about 115 to about 200.

30. The method of claim 16 wherein the acrylic monomer is either methacrylic acid or an amide or ester having the following structures:

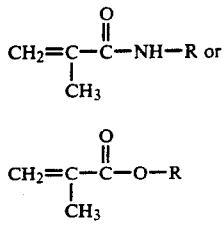

wherein R is an organic radical which provides an overall monomeric molecular weight of from about 115 to about 200.

31. The method of claim 15 wherein the acrylic monomer includes a polyfunctional acrylate which functions to crosslink said polymer.

32. The method of claim 16 wherein the acrylic monomer includes a polyfunctional acrylate which functions to crosslink said polymer.

33. The method of claim 15 wherein the wax has a melting point below about 165° F.

34. The method of claim 16 wherein the wax has a melting point below about 165° F.

35. The method of claim 15 wherein the wax is a paraffin.

36. The method of claim 16 wherein the wax is a paraffin.

37. The method of claim 15 wherein the solvent is an alkane or alkene having from about 6 to 8 carbon atoms.

38. The method of claim 16 wherein the solvent is an alkane or alkene having from about 6 to 8 carbon atoms.

* * * * *